US008452414B2

(12) United States Patent
Poletto

(10) Patent No.: US 8,452,414 B2
(45) Date of Patent: May 28, 2013

(54) STEERING STIMULATION CURRENT BY EMPLOYING STEERING CURRENT

(75) Inventor: Christopher J. Poletto, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 181 days.

(21) Appl. No.: 12/879,928

(22) Filed: Sep. 10, 2010

(65) Prior Publication Data

US 2011/0077717 A1  Mar. 31, 2011

Related U.S. Application Data

(60) Provisional application No. 61/246,910, filed on Sep. 29, 2009.

(51) Int. Cl.
*A61N 1/18* (2006.01)
(52) U.S. Cl.
USPC ............................................................. 607/66
(58) Field of Classification Search
USPC ..................... 607/66, 64, 68–74, 76
See application file for complete search history.

(56) References Cited

U.S. PATENT DOCUMENTS

| 5,036,850 | A | * | 8/1991 | Owens | 607/66 |
|---|---|---|---|---|---|
| 5,111,812 | A | * | 5/1992 | Swanson et al. | 607/2 |
| 5,643,330 | A | * | 7/1997 | Holsheimer et al. | 607/46 |
| 5,895,416 | A |  | 4/1999 | Barreras |  |
| 6,463,330 | B1 | * | 10/2002 | Rabinovitch et al. | 607/67 |
| 6,609,032 | B1 |  | 8/2003 | Woods |  |
| 6,754,539 | B1 |  | 6/2004 | Erickson |  |
| 6,755,694 | B2 | * | 6/2004 | Ries et al. | 439/668 |
| 6,909,917 | B2 |  | 6/2005 | Woods et al. |  |
| 6,993,384 | B2 |  | 1/2006 | Bradley et al. |  |
| 7,212,867 | B2 |  | 5/2007 | Van Venrooij et al. |  |
| 7,363,079 | B1 |  | 4/2008 | Thacker et al. |  |
| 7,491,174 | B2 |  | 2/2009 | Zhu et al. |  |
| 2006/0253182 | A1 |  | 11/2006 | King |  |
| 2008/0046026 | A1 |  | 2/2008 | Pless et al. |  |

FOREIGN PATENT DOCUMENTS

WO  2008142402  11/2008

OTHER PUBLICATIONS

International Search Report for PCT/US2010/049873 mailed Jan. 28, 2011.

* cited by examiner

*Primary Examiner* — Brian T Gedeon
(74) *Attorney, Agent, or Firm* — Withers & Keys, LLC

(57) ABSTRACT

Stimulation current is steered further outward and/or inward from a plane of the stimulating electrodes by using one or more steering currents. The steering current may be used to occupy space in the tissue where stimulation is not desired and to force the stimulation current to pass through target tissue. The steering current may be present in various locations such as in tissue that is immediately adjacent the plane of the electrodes to force the stimulation current away from the immediately adjacent area and deeper into surrounding target tissue. The steering current may be present in tissue that is beyond the target tissue to confine the outward reach of the stimulation current to that target tissue. The stimulation current may be produced by one power source while the steering current may be produced by one or more other power sources, each of the power sources being unreferenced to each other.

37 Claims, 7 Drawing Sheets

STEERING STIMULATION CURRENT BY EMPLOYING STEERING CURRENT

RELATED APPLICATIONS

The present application claims priority to U.S. Provisional Application 61/246,910, entitled STEERING STIMULATION CURRENT BY EMPLOYING STEERING CURRENT, filed on Sep. 29, 2009, which is incorporated by reference herein.

TECHNICAL FIELD

Embodiments relate to current steering for implantable medical devices. More particularly, embodiments relate to steering stimulation current by employing steering current in addition to the stimulation current.

BACKGROUND

Implantable medical devices may provide stimulation current to a stimulation site within a body of a patient to excite certain tissues to treat a medical condition. In some cases, the area to be stimulated may require a degree of precision such as where stimulating surrounding tissue is undesirable. Furthermore, due to physiological constraints on where electrodes can be positioned, the particular tissue to be stimulated may not be immediately adjacent the electrodes that provide the stimulation current.

Conventional current steering techniques include the transverse tripole, which is used for spinal cord stimulation. The transverse tripole uses two anodes and a central cathode place at the midline of the spinal column. Two simultaneous stimulation pulses of different amplitudes are provided via this tripole configuration, which has the effect of shielding lateral tissues from receiving stimulation and focusing the stimulation current relative to the midline.

While the transverse tripole configuration may provide a degree of stimulation current steering relative to the midline, the issues noted above are not addressed. Namely, the transverse tripole configuration does not push the stimulation current deeper into the tissue without a corresponding increase in stimulation current magnitude, where such an increase in magnitude creates increased stimulation also in the immediate vicinity of the electrodes. Thus, the transverse tripole configuration does not address situations where the tissue immediately adjacent the electrodes should not be stimulated.

Furthermore, such conventional efforts at current steering do not prevent the stimulation current from penetrating beyond the targeted tissue. Therefore, stray stimulation current may also provide unwanted stimulation to tissues beyond the targeted tissue.

SUMMARY

Embodiments address issues such as these and others by providing steering of stimulation current by using one or more steering currents. The steering current may be used to occupy space in the tissue where stimulation is not desired and to force the stimulation current to pass through target tissue where the stimulation is desired. The steering current may be present in tissue that is immediately adjacent the electrode area to force the stimulation current away from the tissue in the immediately adjacent area and deeper into surrounding target tissue. The steering current may also be present in tissue that is beyond the target tissue to confine the outward reach of the stimulation current to that target tissue.

Embodiments provide a method of steering current to stimulate tissue. The method involves generating a first current through tissue and between a first electrode and a second electrode, the first electrode and second electrode being referenced to a first power source. While generating the first current, the method further involves generating a second current through tissue and between a third electrode and a fourth electrode, the third electrode and the fourth electrode being referenced to a second power source that is not referenced to the first power source, the first and second electrodes being positioned between the third and fourth electrodes.

The first current may be a stimulation current and the second current may be a steering current that limits an outward reach of the stimulation current. The stimulation current may be of various forms such as a train of pulses and the steering current may be of various forms such as a square-wave. The steering current may be present only when the stimulation current is present. The second current may instead be a stimulation current, and the first current may instead be a steering current that increases an outward reach of the stimulation current.

The first, second, third, and fourth electrodes may be of various forms such as concentric circles, with the third electrode having a smallest diameter and the fourth electrode having the largest diameter. The first, second, third and fourth electrodes may be of other forms such as ring electrodes along a lead body. The first and second electrodes may instead be present on a paddle, be of various shapes such as rectangular, and have a first length. Likewise, the third and fourth electrodes may also be present on the paddle, be of various shapes such as rectangular, and have a second length that is more than twice the first length when providing steering current or less than half of the first length when providing stimulation current.

While generating the first and second currents, the method may further involve generating a third current through tissue and between a fifth electrode and a sixth electrode. The fifth electrode and the sixth electrode may be referenced to a third power source that is not referenced to the first and second power sources. The first, second, third, and fourth electrodes may be located between the fifth and sixth electrodes, the third current being a second steering current that limits an outward reach of the stimulation current. The fifth and sixth electrodes may instead be located between the first, second, third, and fourth electrodes, the third current being a second steering current that increases an outward reach of the stimulation current.

The steering current may have a frequency that is greater than a frequency of the stimulation current such that the steering current does not excite the tissue. Likewise, the second steering current when present may have a frequency that is greater than a frequency of the stimulation current such that the steering current and the second steering current do not excite the tissue.

Embodiments provide for an implantable medical device that includes a first power source and a second power source not referenced to the first power source. The implantable medical device further includes a first and a second electrical connector referenced to the first power source such that a first current from the first power source flows between the first and second electrical connectors. The implantable medical device further includes a third and a fourth electrical connector referenced to the second power source such that a second current from the second power source flows between the third and fourth electrical connectors.

The implantable medical device may further include at least one electrical lead. The electrical lead includes a first electrode electrically coupled to the first electrical connector, a second electrode electrically coupled to the second electrical connector, a third electrode electrically coupled to the third electrical connector, and a fourth electrode electrically coupled to the fourth electrical connector, wherein the first and second electrodes are located between the third and fourth electrodes.

The first current of the implantable medical device may be a stimulation current and the second current of the implantable medical device may be a steering current that limits an outward reach of the stimulation current. The stimulation current of the implantable medical device may be of various forms such as a train of pulses, and the steering current of the implantable medical device may also be of various forms such as a squarewave. The steering current of the implantable medical device may be present only when the stimulation current is present. The second current of the implantable medical device may instead be a stimulation current and the first current of the implantable medical device may instead be a steering current that increases an outward reach of the stimulation current.

The first, second, third, and fourth electrodes of the implantable medical device may be of various forms such as concentric circles, with the third electrode having a smallest diameter and the fourth electrode having the largest diameter. The first, second, third and fourth electrodes may instead be ring electrodes along a body of the lead. The first and second electrodes may instead be present on a paddle, may be of various shapes such as rectangular, and have a first length. Likewise, the third and fourth electrodes may be present on the paddle, may be of various shapes such as rectangular, and have a second length that is more than twice the first length when providing steering current and have a second length that is less than half of the first length when providing stimulation current.

The implantable medical device may further include a third power source not referenced to the first and second power sources. The implantable medical device may also include a fifth and a sixth electrical connector referenced to the third power source such that a third current from the third power source flows between the fifth and sixth electrical connectors. The lead may further include a fifth electrode electrically coupled to the fifth electrical connector and a sixth electrode electrically coupled to the sixth electrical connector. The first, second, third, and fourth electrodes may be located between the fifth and sixth electrodes, the third current being a second steering current that limits an outward reach of the stimulation current. The fifth and sixth electrodes may instead be located between the first, second, third, and fourth electrodes, with the third current being a second steering current that increases an outward reach of the stimulation current.

The steering current of the implantable medical device may have a frequency that is greater than a frequency of the stimulation current such that the steering current does not excite the tissue. The second steering current when present may also have a frequency that is greater than a frequency of the stimulation current such that the steering current and the second steering current do not excite the tissue.

Embodiments provide for a method of providing stimulation therapy. The method involves sending programming from an external device to an implantable medical device, the programming specifying stimulation parameters and steering current parameters. While stimulation signals are being output from a first power source of the implantable medical device to leads coupled to the implantable medical device in accordance with the stimulation parameters, the implantable medical device outputs at least one steering current from a second power source that is unreferenced to the first power source in accordance with the steering current parameters.

Embodiments provide for a system of providing stimulation therapy. The system includes an external device that sends programming that specifies stimulation parameters and steering current parameters. An implantable medical device receives the programming and outputs stimulation signals from a first power source according to the stimulation parameters. While outputting the stimulation signals from the first power source, the implantable medical device outputs at least one steering current from a second power source that is unreferenced to the first power source in accordance with the steering current parameters.

DETAILED DESCRIPTION

Embodiments provide for steering of stimulation current being output by an implantable medical device by employing steering current. The steering current may be present to force the stimulation current further into the tissue and away from the stimulation electrode pair and/or to restrict the stimulation current from extending further into the tissue than is desired. The steering current may be of a frequency selected to impart no stimulation to the tissue where the steering current is present.

Figure 1:
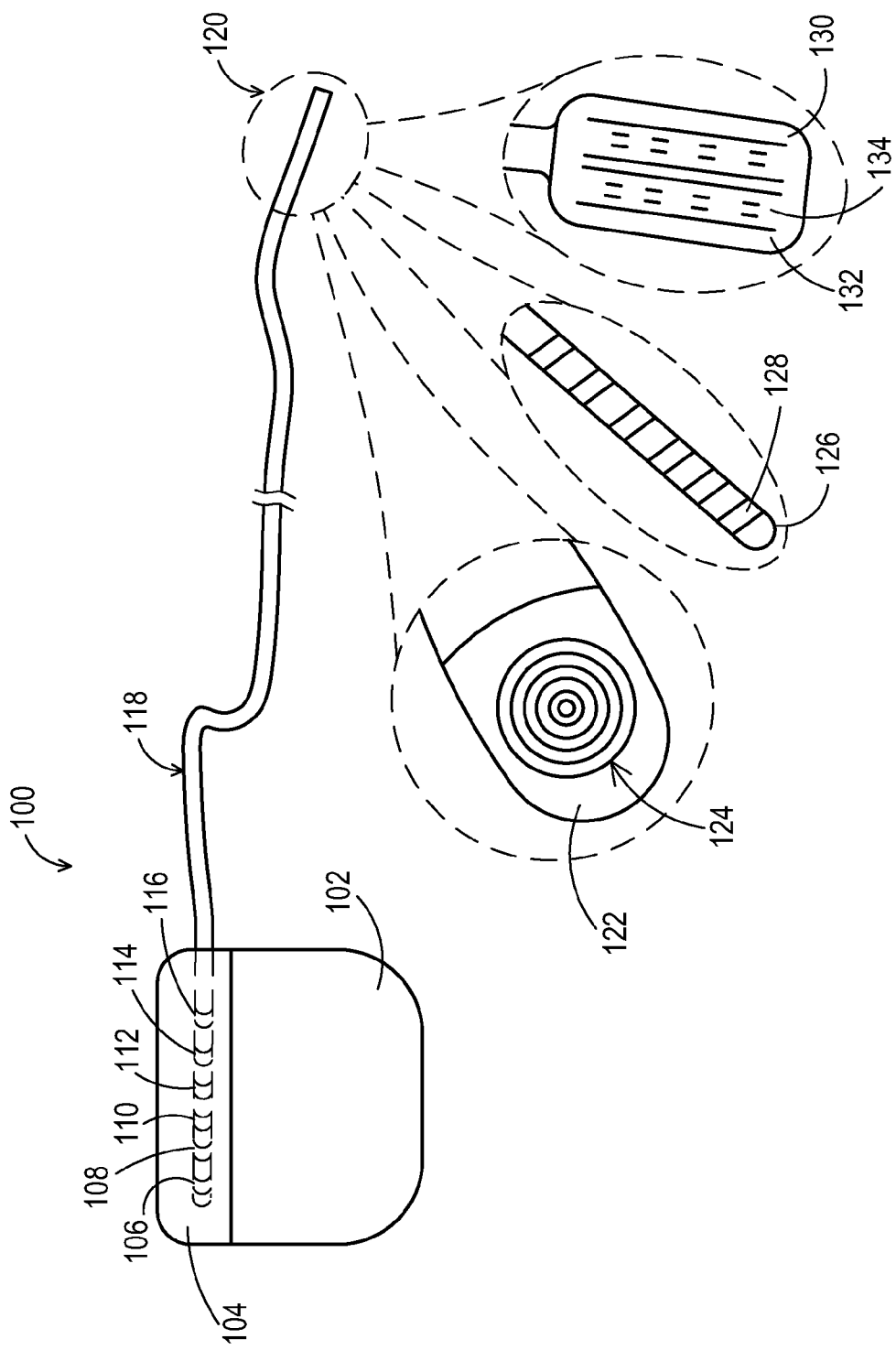
FIG. 1 shows an example of an implantable medical device and various lead types.

FIG. 1 shows an example of an implantable medical device (IMD) 100. The IMD 100 includes a can 102 that houses the electrical circuitry used to create stimulation and steering currents. The IMD 100 includes a connector block module 104 where several electrical connectors are present to transfer the stimulation and steering currents to a medical lead 118 that has a proximal end installed in the connector block module 104. In this particular example, three pairs of electrical connectors 106, 108, 110, 112, 114, and 116 are present. The medical lead 118 includes conductors that carry the stimulation and steering currents to a distal area 120 which is implanted at a stimulation site within the body of the patient. Each connector 106, 108, 110, 112, 114, and 116 has a corresponding electrical conductor within the lead 118 and a corresponding electrode in the distal area 120.

The distal area 120 may utilize one of various different types of configurations. Some examples of the configurations are also shown in FIG. 1. For instance, the distal area 120 may include a concentric configuration 122 where a collection of circular and concentric electrodes 124 are present at a flat surface of the lead 118. This concentric configuration 122 is discussed in more detail below with reference to FIG. 4. As another example, the distal area 120 may be a percutaneous configuration 126 whereby a series of ring electrodes 128 are present. This percutaneous configuration 126 is discussed in more detail below with reference to FIG. 6. FIG. 1 also shows an example of a paddle configuration 130 at the distal area 120, where the paddle configuration 130 includes a series of long electrodes 132 and short electrodes 134. The paddle configuration 130 is discussed in more detail below with reference to FIG. 5.

Figure 2:
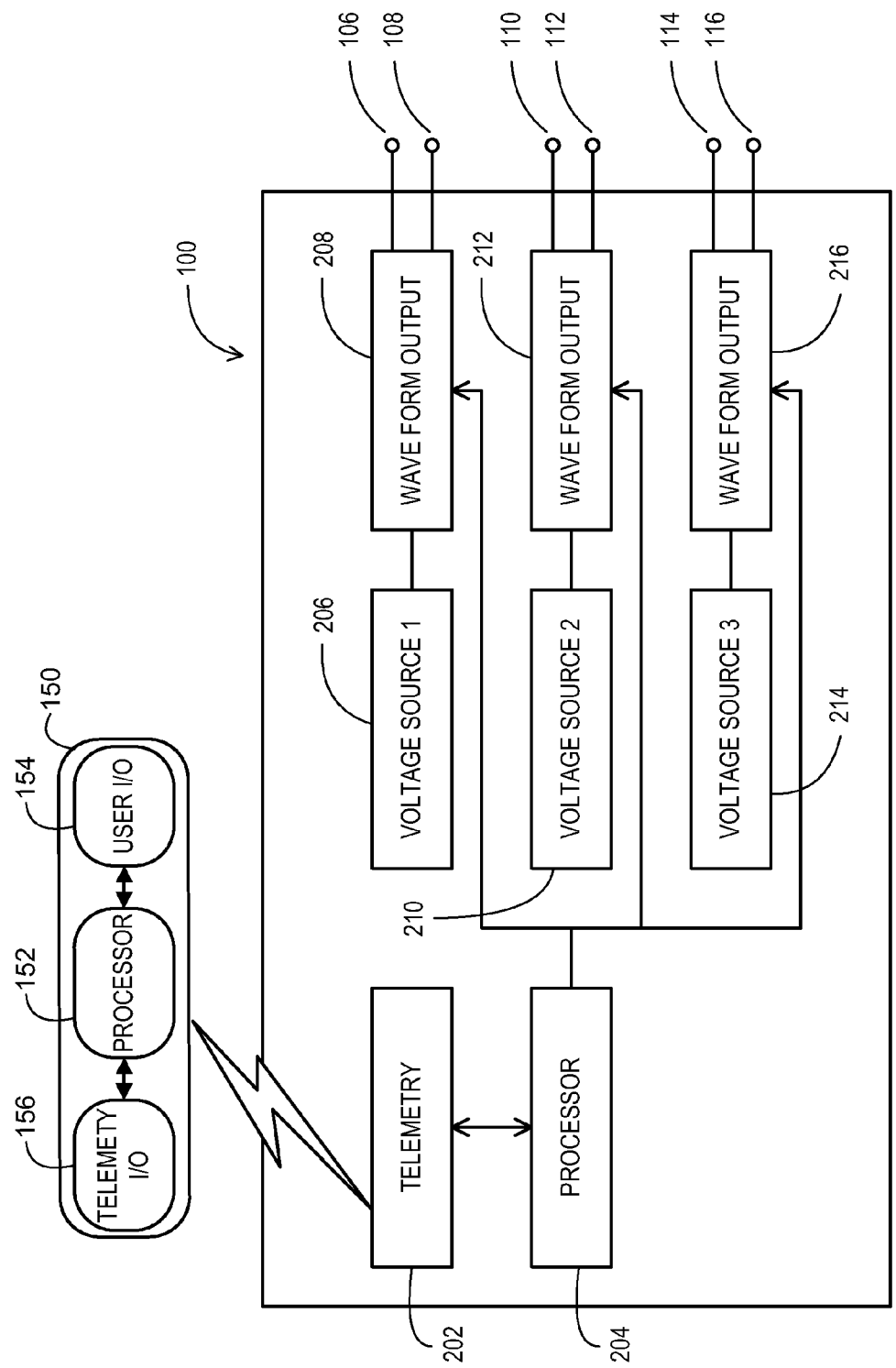
FIG. 2 shows a block diagram of an example of the implantable medical device and a related external programmer.

FIG. 2 shows a block diagram of one example of the IMD 100. The IMD 100 may include a telemetry module 202 that allows the IMD 100 to exchange information wirelessly with an external programming device 150. The telemetry module 202 may employ near field, arm's length, or longer range radio frequency signaling to exchange the information. The information may include stimulation therapy programming. This programming may include parameters for the stimulation current and may also include parameters for the steering current.

A processor 204 communicates with the telemetry module 202 to exchange the information. The processor 204 may then implement the stimulation therapy programming by communicating with the components that produce the stimulation and steering waveforms. The processor 204 may program control registers to specify parameters for waveform generation including pulse width and rate for the stimulation current, frequency for the steering current, amplitudes, waveform shape, and so forth.

The processor 204 may be implemented in various forms, such as a dedicated purpose processor, a general purpose programmable processor, hardwired digital logic, and combinations thereof. The processor 204 may utilize volatile and/or non-volatile memory that is integrated or is a separate component to store operational programming, stimulation therapy parameter values, steering current parameter values, and other information.

The IMD 100 also includes multiple power sources, which could be voltage sources or current sources that are unreferenced to each other. In the example shown, the IMD 100 is capable of producing two different steering currents in addition to the stimulation current and includes a separate voltage source 206, 210, and 214 for each of the three currents. However, it will be appreciated that the voltage sources may alternatively be current sources, although voltage sources are shown and described for illustration. Additionally, stimulation current may be steered to some extent by a single steering current and in that case, two separate voltage sources are present rather than three. As one example of separate voltage sources that are unreferenced to each other, the separate voltage sources 206, 210, and 214 may be separate batteries that produce voltages that are floating relative to one another.

Each voltage source 206, 210, and 214 provides power to a respective waveform output circuit 208, 212, and 216. Each waveform output circuit 208, 212, and 216 receives instructions from the processor 204 about the waveform parameters. The waveform output circuits 208, 212, and 216 then produce an output across a respective pair of electrical connectors 106/108, 110/112, and 114/116 that are present within the connector module block 104 to distribute the stimulation current and steering currents to the medical lead 118.

The external programmer 150 may include components such as a processor 152, user input/output devices 154, and a telemetry module 156. The processor 152 may provide a user interface that allows a user such as a clinician or patient to set parameters for the stimulation therapy. A user may specify stimulation parameters such as a pulse rate, width, and magnitude. The user may also specify parameters for the steering current, such as how many steering currents to employ as well as the frequency and magnitude of the steering current or rely on logic of the processor 152 to define steering current parameters based on stimulation current parameters.

The processor 152 may communicate the programming for stimulation therapy and steering currents to the telemetry module 202 of the IMD 100 through a telemetry module 156. The telemetry module 156 exchanges information with the telemetry module 202 of the IMD 100 via wireless signals.

The processor 152 may be implemented in various forms, such as a dedicated purpose processor, a general purpose programmable processor, hardwired digital logic, and combinations thereof. The processor 152 may utilize volatile and/or non-volatile memory that is integrated or is a separate component to store operational programming, stimulation therapy parameter values, steering current parameter values, and other information.

Figure 3A:
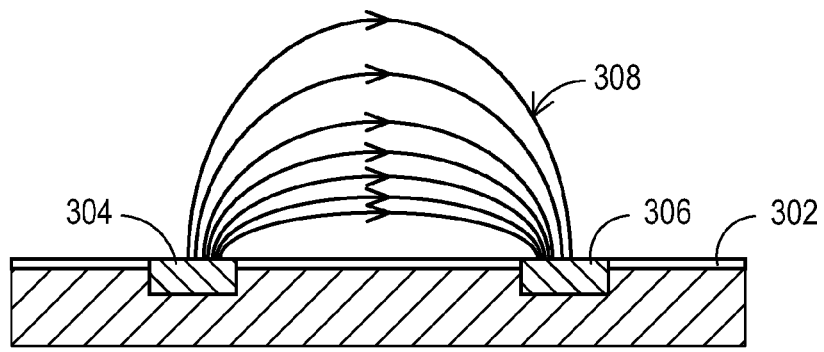
FIG. 3A shows a stimulation current when steering current is not present.
Figure 3B:
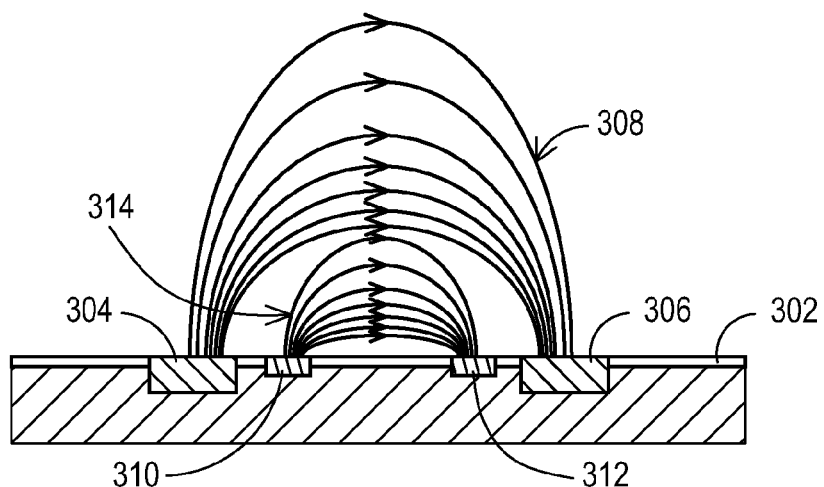
FIG. 3B shows the stimulation current when a first steering current is present to urge the stimulation current outward.
Figure 3C:
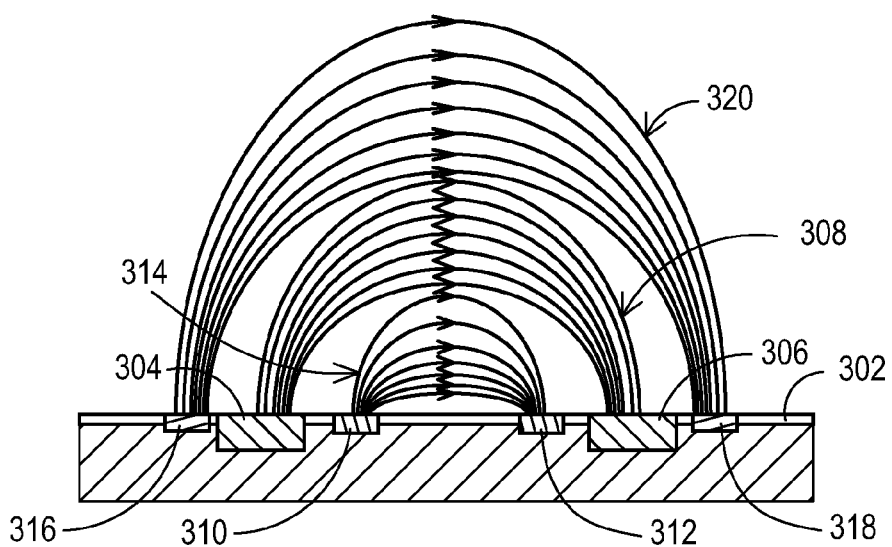
FIG. 3C shows the stimulation current when the first steering current is present along with a second steering current that limits the outward reach of the stimulation current.

FIGS. 3A-3C illustrate the electric field(s) and current flux that are present in the tissue and that are established by the potential differences between electrode pairs. The direction of the current flow at any point on a line is tangent to the line, with closer spacing of the lines indicating higher current density. For simplicity, the tissue is assumed to be a homogeneous and isotropic conductor so that the lines of current flux have patterns identical to the electric field lines. Also, the current lines are everywhere perpendicular to lines of constant electric potential (not shown). In FIG. 3A, no electric fields for steering current are present. In FIG. 3B, an electric field for a single steering current is present, and in FIG. 3C, two electric fields corresponding to two steering currents are present.

In FIG. 3A, a pair of stimulation electrodes 304, 306 are present within an insulator 302, such as an outer surface of the lead body 118. A voltage potential exists between the electrode pair 304/306 resulting in a collection of electric field lines 308. Electrical current, in this case stimulation current, flows along the electric field lines. As can be seen, the electric field lines 308, and hence the stimulation current, are free to pass through the tissue as close to the insulator 302 and as far away from the insulator 302 as the stimulation signal magnitude allows.

In situations where there is excitable tissue closer to the insulator 302 than the target tissue to be stimulated, the situation in FIG. 3A can be problematic. The stimulation current density may be greater at the tissue that is closer to the insulator 302 and that should not be stimulated than at the target tissue resulting in substantial unwanted stimulation. Likewise, there may be tissue that should not be stimulated that is farther away from the insulator 302 than the target tissue, and some stimulation current may reach out to such tissue at levels high enough to cause unwanted stimulation.

FIG. 3B shows a configuration where a steering electrode pair 310, 312 is placed between the two stimulation electrodes 304, 306. A voltage potential exists between the steering electrode pair 310, 312 to produce electric field lines 314 within the tissue and thus there is a steering current that is present along those electric field lines 314.

Because the voltage source providing the voltage potential between the stimulation electrode pair 304, 306 is unreferenced to the voltage source providing the voltage potential between the steering electrode pair 310, 312, the electric field lines 308 and 314 do not cross and therefore do not occupy the same physical space within the tissue. As a result, the electric field lines 308 of the stimulation current no longer occupy the space close to the electrode pairs 304, 306 but are instead pushed outward into the region where the target tissue is located. This effect is not dependent upon the direction of either of the currents. It will be appreciated that the relative magnitudes of the currents will impact the degree to which the steering current reaches outward from the insulator 302 to force the electric field lines 308 away from the insulator 302.

The portion of the electric field lines 308 that emanate directly from the electrodes 304, 306 in a relatively orthogonal relationship to the insulator 302 pass through the immediately adjacent tissue. However, this portion of the electric field lines 308 has no impact on nerve tissue with the axis of the axons running parallel to the surface of the insulator 302. Thus, any nerve tissue present near the electrodes 304, 306 that have axons with an axis running parallel to the surface 302 are not stimulated by the stimulation current of the electric field lines 308. However, where the surface of the insulator 302 is parallel to a nerve fiber to be stimulated, those lines of electric field 308 that are tangent to the surface of the insulator 302, and hence tangent to the nerve fiber to be stimulated, provide stimulation to the nerve fiber as desired. Those electric field lines 308 that are tangent to the surface of the insulator 302 are controlled by the steering current of the electric field lines 314.

Additionally, the steering current of the electric field lines 314 may change polarity at a rate that is sufficiently high so that voltage gated channels in the tissue do not have time to respond. Thus, no excitement of that tissue receiving the steering current occurs as the steering current neither depolarizes nor hyperpolarizes the excitable membrane of the tissue. The steering current may have the form of a square-wave or other similar waveform that changes polarity. The frequency of the waveform may be in excess of 10 kilohertz, such as on the order of 100 kilohertz, but is maintained at a frequency that is low enough to avoid excessive heating of the tissue.

FIG. 3C shows another configuration whereby another pair of steering electrodes 316, 318 are present, with the stimulation electrode pair 304, 306 and the inner steering electrode pair 310, 312 being located between the electrodes 316 and 318. The additional steering electrode pair 316, 318 receives power from another voltage source that is unreferenced to the voltage source of the inner steering electrode pair 310, 312 and also unreferenced to the voltage source of the stimulation electrode pair 304, 306.

The electrode pair 316, 318 produces a collection of electric field lines 320 along which additional steering current is provided. The electric field lines 320 extend beyond the electric field lines 308 of the stimulation current. Because the voltage source providing the voltage potential between the stimulation electrode pair 304, 306 is unreferenced to the voltage source providing the voltage potential between the steering electrode pair 316, 318, the electric field lines 308 and 320 do not cross and therefore do not occupy the same physical space within the tissue. As a result, the electric field lines 308 of the stimulation current no longer occupy the space farther outward than the target tissue but are instead pushed inward into the region where the target tissue is located. This effect is also not dependent upon the direction of either of the currents. It will be appreciated that the relative magnitudes of the currents will impact the degree to which the steering current of the electric field lines 320 reaches outward from the insulator 302 to force the electric field lines 308 of the stimulation current toward from the insulator 302.

As can be seen in FIG. 3C, the electric field lines 314 and 320 of the steering currents squeeze the electric field lines 308 of the stimulation current into a tight band that passes through a desired region at a particular distance from the insulator 302. As such, the stimulation current is being focused through the target tissue while being pushed beyond untargeted tissue near the insulator 302 and pushed inward from untargeted tissue beyond the targeted tissue. The relative magnitudes of the steering and stimulation currents may be titrated to obtain the desired effect of the stimulation.

Figure 4:
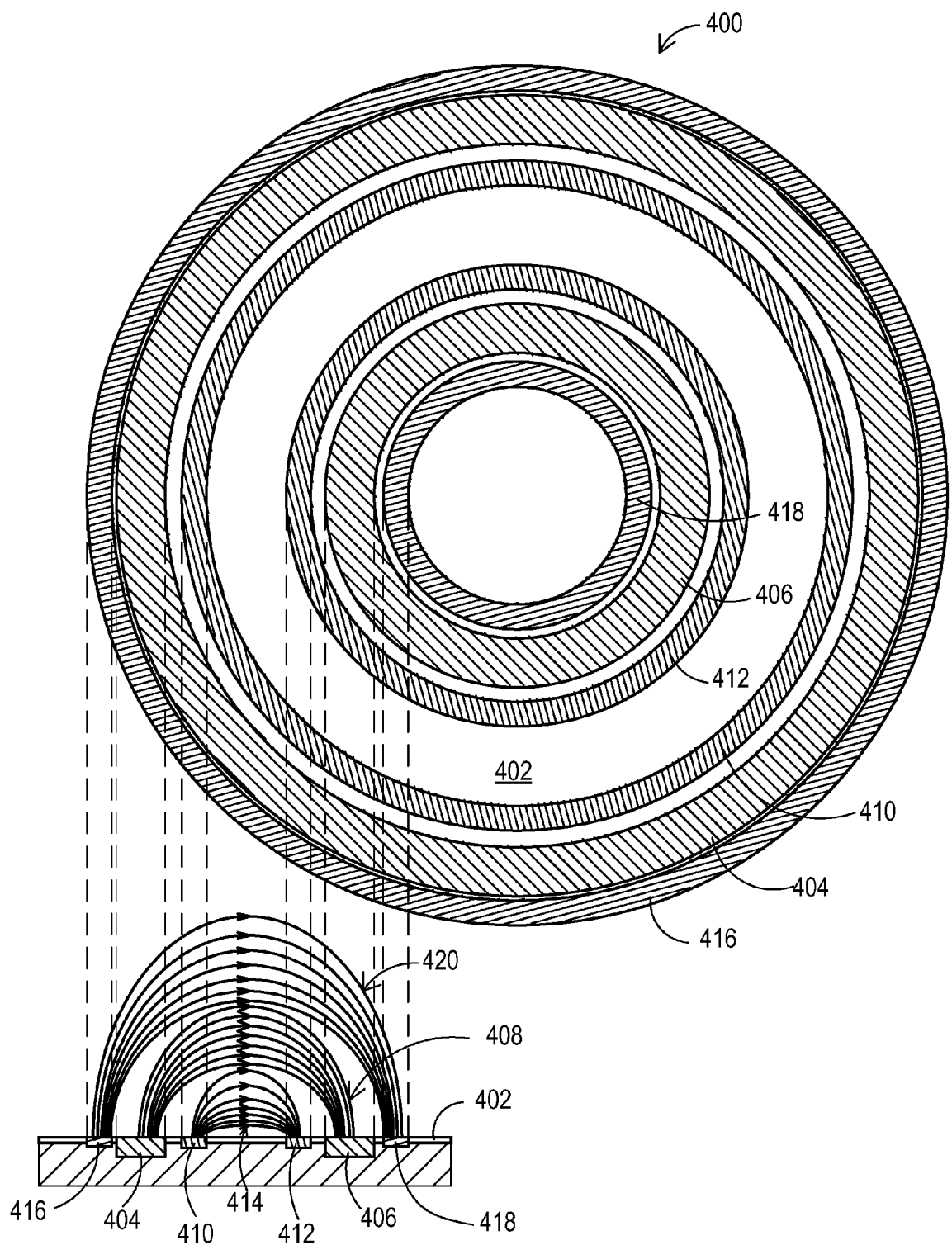
FIG. 4 shows an example of a circular stimulation electrode pair surrounded by first and second steering electrode pairs.

FIG. 4 shows an example of a concentric configuration 400 that includes two pairs of steering electrodes for a pair of stimulation electrodes within an insulator 402. One pair of steering electrodes 410, 412 produces electric field lines 414 for steering current. Another pair of steering electrodes 416, 418 produces electric field lines 420 for another steering current. A pair of stimulation electrodes 404, 406 is situated such that the electric field lines 408 of the stimulation current are trapped between the electric field lines 414 and 420 of the steering currents. The electric field lines 408, 414, and 420 at their peak point in the radial direction and are present entirely around the circle to form halved toroids. Therefore, the stimulation current remains trapped between the two steering currents about the entire circle.

It will be appreciated that embodiments of the concentric configuration may vary from the one discussed above. For instance, in another example, only a single pair of steering electrodes may be present to either push the stimulation current outward or to push the stimulation current inward. Other numbers of steering electrode pairs and/or stimulation electrode pairs may also be applied. Additionally, in some examples, the stimulation electrodes may be segmented rather than being complete circles.

Furthermore, in other examples, there may be multiple pairs of stimulation electrodes present such as where electrode pair 410, 412 and electrode pair 416, 418 are stimulation electrodes rather than steering electrodes. In such an example, the electrode pair 404, 406 provides steering current rather than stimulation current so that the electric field lines 408 force stimulation field lines 420 outward while forcing stimulation field lines 414 inward.

Figure 5:
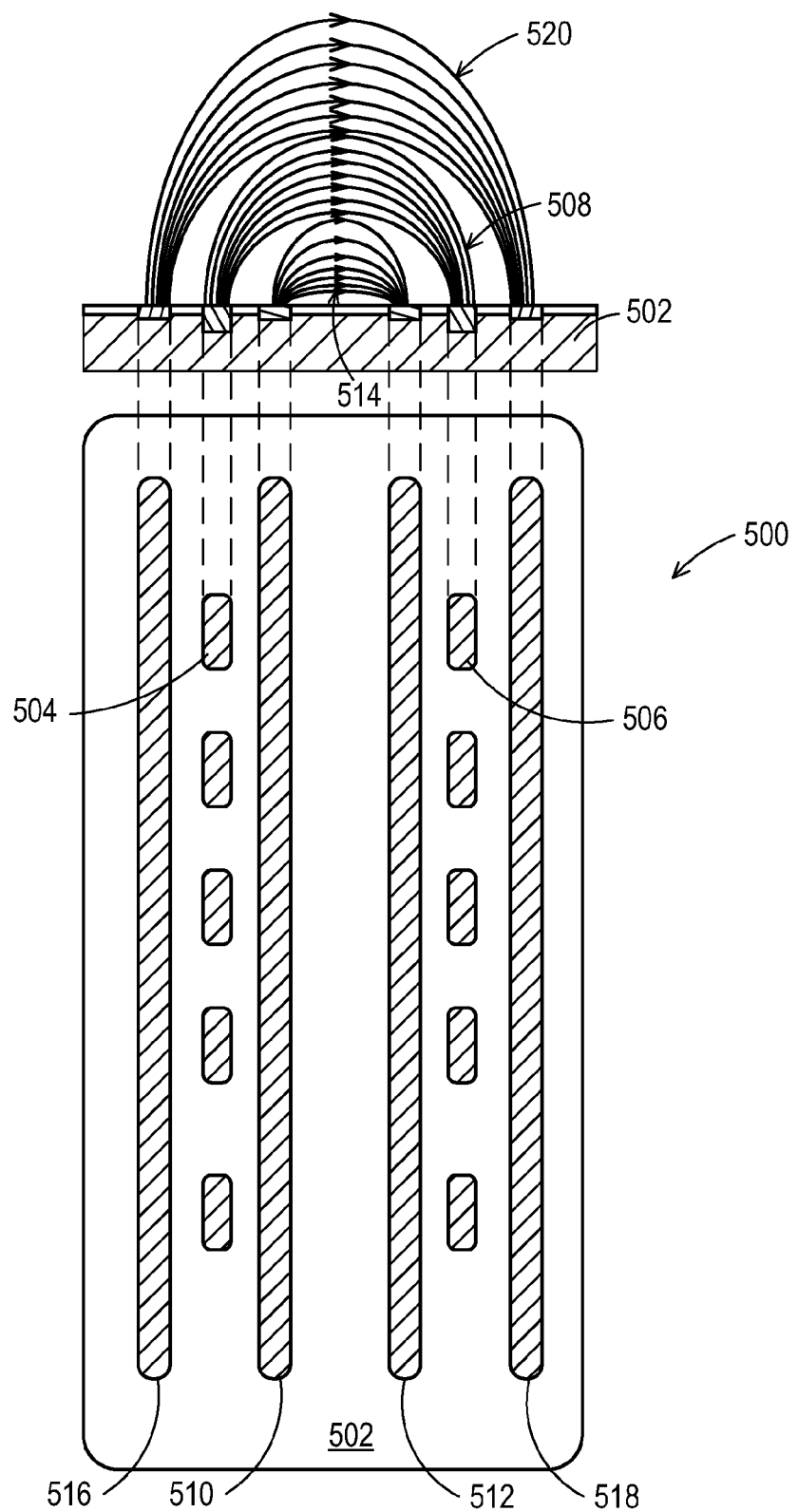
FIG. 5 shows an example of an electrode paddle that includes a stimulation electrode pair surrounded by first and second steering electrode pairs.

FIG. 5 shows an example of a paddle configuration 500 that includes two pairs of steering electrodes for multiple pairs of stimulation electrodes within an insulator 502. It will be appreciated that only a single pair of stimulation electrodes may be in use at any given time or that multiple pairs may be in use. One pair of steering electrodes 510, 512 produces electric field lines 514 for steering current. Another pair of steering electrodes 516, 518 produces electric field lines 520 for another steering current. A pair of stimulation electrodes 504, 506 is situated such that the electric field lines 508 of the stimulation current are trapped between the electric field lines 514 and 520 of the steering currents. The electric field lines 508, 514, and 520 at their peak point in the transverse direction of the paddle. Furthermore, because the steering electrodes 510, 512, 516, and 518 are substantially longer than the stimulation electrodes 504, 506, such as more than twice as long, the stimulation current remains trapped along the lengths of the steering electrodes 510, 512, 516, and 518.

It will be appreciated that embodiments of the paddle configuration may vary from the one discussed above. For instance, in one example, only a single pair of steering electrodes is present to either push the stimulation current outward or to push the stimulation current inward. Other numbers of steering electrode pairs and/or stimulation electrode pairs may also be applied.

Furthermore, in other examples, there may be multiple pairs of stimulation electrodes present such as where electrode pair 516, 518 and electrode pair 510, 512 are shorter and become stimulation electrodes rather than steering electrodes. In such an example, the electrode pair 504, 506 may be longer than the stimulation electrode pairs and provides steering current rather than stimulation current so that the electric field lines 508 force stimulation field lines 520 outward while forcing stimulation field lines 514 inward.

Figure 6:
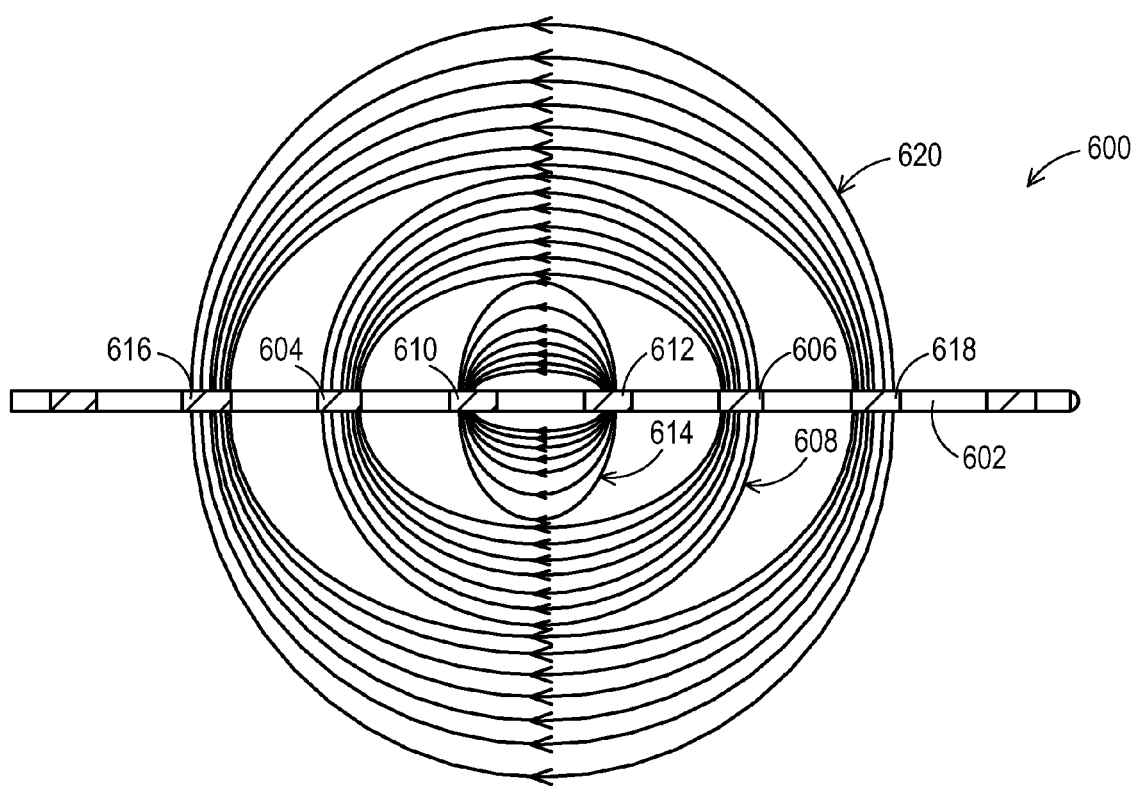
FIG. 6 shows an example of a percutaneous lead that includes a stimulation ring electrode pair surrounded by first and second steering ring electrode pairs.

FIG. 6 shows an example of a percutaneous configuration 600 that includes two pairs of steering electrodes for a pair of stimulation electrodes within an insulator 602. One pair of steering electrodes 610, 612 produces electric field lines 614 for steering current. Another pair of steering electrodes 616, 618 produces electric field lines 620 for another steering current. A pair of stimulation electrodes 604, 606 is situated such that the electric field lines 608 of the stimulation current are trapped between the electric field lines 614 and 620 of the steering currents. The electric field lines 608, 614, and 620 at their peak point in the longitudinal direction of the lead body and encircle the lead body to the extent the electrodes 604, 606, 610, 612, 616, and 618 fully encircle the lead body. Furthermore, because the steering electrodes 610, 612, 616, and 618 fully encircle the lead body, the stimulation current remains trapped at the set distance about the lead body.

It will be appreciated that embodiments of the percutaneous configuration may vary from the one discussed above. For instance, in one example, only a single pair of steering electrodes is present to either push the stimulation current outward or to push the stimulation current inward. Other numbers of steering electrode pairs and/or stimulation electrode pairs may also be applied. Additionally, in some examples, the stimulation electrodes may be segmented rather than fully encircling the lead body.

Furthermore, in other examples, there may be multiple pairs of stimulation electrodes present such as where electrode pair 610, 612 and electrode pair 616, 618 are stimulation electrodes rather than steering electrodes. In such an example, the electrode pair 604, 606 provides steering current rather than stimulation current so that the electric field lines 608 force stimulation field lines 620 outward while forcing stimulation field lines 614 inward.

Figure 7:
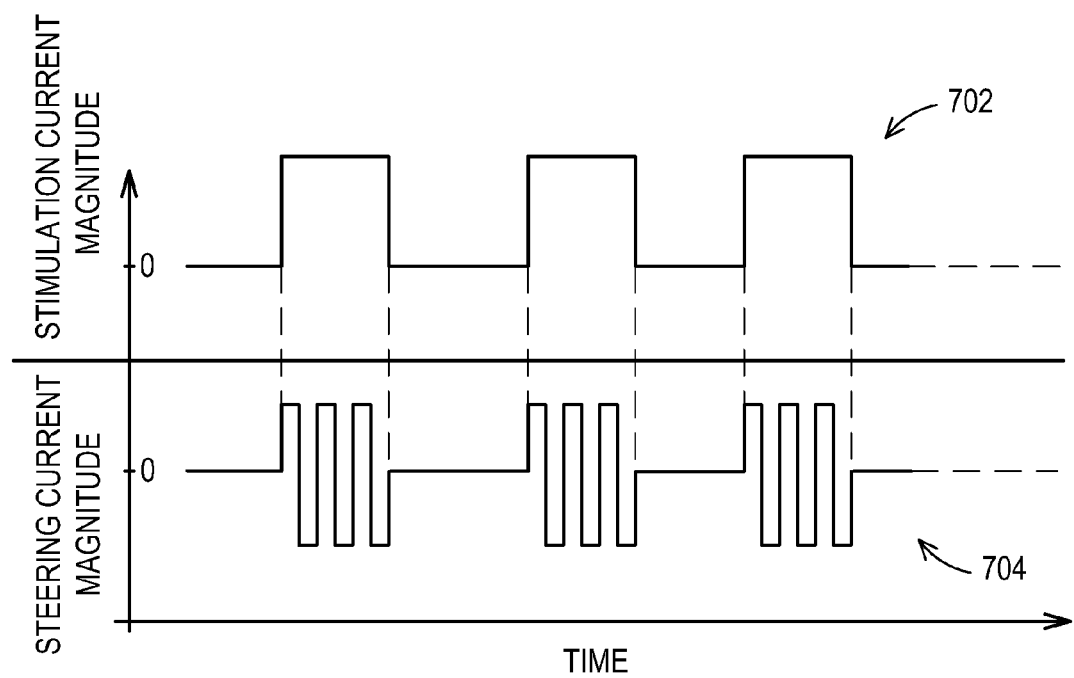
FIG. 7 shows a timeline for the magnitude of the stimulation current and the steering current waveforms.

FIG. 7 shows an example of a magnitude of stimulation and steering signals over time. In this example, the stimulation signal is a pulse at a given rate and width. To increase efficiency of the IMD 100, this example provides for switching the steering current(s) off between pulses of the stimulation signal. During a pulse of the stimulation signal, the steering current is an active squarewave that reverses polarity at a rate sufficiently high to avoid stimulation of tissue but sufficiently low to avoid excessive heating. During the time the stimulation signal is at zero, the steering signal may remain at zero as well. It will be appreciated that the frequency of the squarewave relative to the width of the pulse of the stimulation current is not shown at an actual scale for purposes of clarity and that the frequency of the squarewave may be significantly higher than that shown. It will also be appreciated that where multiple steering currents are present, they may differ in frequency and/or phase.

In one embodiment, the relative magnitudes of the steering and/or stimulation currents may be changed from one pulse to the next pulse to change the reach of the stimulation current from the plane of the electrodes so that more than one target tissue region is affected by the stimulation current. For example, during a first stimulation pulse, the steering current may have a first amplitude that steers the stimulation pulse into a first target tissue region. During a second subsequent stimulation pulse, the steering current may have a second amplitude that is different from the first amplitude to direct the stimulation pulse towards a second target tissue region different than the first target tissue region. In this manner, by varying amplitudes of one or more steering currents and/or the amplitude of the stimulation current from one pulse to the next, different tissue regions may be stimulated in a time-interleaved manner.

While embodiments have been particularly shown and described, it will be understood by those skilled in the art that various other changes in the form and details may be made therein without departing from the spirit and scope of the invention.

What is claimed is:

1. A method of steering current to stimulate tissue by an implantable medical device, comprising:
   generating at the implantable medical device a first current through tissue and between a first electrode and a second electrode, the first electrode and second electrode being referenced to a first voltage source; and
   while generating the first current, generating at the implantable medical device a second current through tissue and between a third electrode and a fourth electrode, the third electrode and the fourth electrode being referenced to a second voltage source that is not referenced to the first voltage source, the first and second electrodes being positioned between the third and fourth electrodes.

2. The method of claim 1, wherein the first current is a stimulation current and the second current is a steering current that limits an outward reach of the stimulation current.

3. The method of claim 2, wherein the stimulation current is a train of pulses and the steering current is a squarewave.

4. The method of claim 2, wherein the steering current is present only when the stimulation current is present.

5. The method of claim 2, wherein the first and second electrodes are present on a paddle, are rectangular, and have a first length and the third and fourth electrodes are present on the paddle, are rectangular, and have a second length that is more than twice the first length.

6. The method of claim 2, further comprising:
   while generating the first and second currents, generating at the implantable medical device a third current through tissue and between a fifth electrode and a sixth electrode, the fifth electrode and the sixth electrode being referenced to a third voltage source that is not referenced to the first and second voltage sources, the fifth and sixth electrodes being located between the first and second electrodes, the third current being a second steering current that increases an outward reach of the stimulation current.

7. The method of claim 6, wherein the steering current and the second steering current have a frequency that is greater than a frequency of the stimulation current such that the steering current and the second steering current do not depolarize the tissue.

8. The method of claim 2, wherein the steering current has a frequency that is greater than a frequency of the stimulation current such that the steering current does not depolarize the tissue.

9. The method of claim 1, wherein the second current is a stimulation current and the first current is a steering current that increases an outward reach of the stimulation current.

10. The method of claim 9, wherein the stimulation current is a train of pulses and the steering current is a squarewave.

11. The method of claim 9, wherein the steering current is present only when the stimulation current is present.

12. The method of claim 9, wherein the first and second electrodes are rectangular and have a first length and the third and fourth electrodes are rectangular and have a second length that is less than half of the first length.

13. The method of claim 9, further comprising:
while generating the first and second currents, generating at the implantable medical device a third current through tissue and between a fifth electrode and a sixth electrode, the fifth electrode and the sixth electrode being referenced to a third voltage source that is not referenced to the first and second voltage sources, the first, second, third, and fourth electrodes being located between the fifth and sixth electrodes, the third current being a second steering current that limits an outward reach of the stimulation current.

14. The method of claim 13, wherein the steering current and the second steering current have a frequency that is greater than a frequency of the stimulation current such that the steering current and the second steering current do not depolarize the tissue.

15. The method of claim 9, wherein the steering current has a frequency that is greater than a frequency of the stimulation current such that the steering current does not depolarize the tissue.

16. The method of claim 1, wherein the first, second, third, and fourth electrodes are concentric circles, with the third electrode having a smallest diameter and the fourth electrode having a largest diameter.

17. The method of claim 1, wherein the first, second, third and fourth electrodes are ring electrodes along a lead body.

18. An implantable medical device, comprising:
a first voltage source;
a second voltage source not referenced to the first voltage source;
a first and a second electrical connector referenced to the first voltage source such that a first current from the first voltage source flows between the first and second electrical connectors;
a third and a fourth electrical connector referenced to the second voltage source such that a second current from the second voltage source flows between the third and fourth electrical connectors;
wherein the first current is a stimulation current and the second current is a steering current that limits an outward reach of the stimulation current, and wherein the steering current has a frequency that is greater than a frequency of the stimulation current such that the steering current does not depolarize the tissue.

19. An implantable medical device, comprising:
a first voltage source;
a second voltage source not referenced to the first voltage source;
a first and a second electrical connector referenced to the first voltage source such that a first current from the first voltage source flows between the first and second electrical connectors; and
a third and a fourth electrical connector referenced to the second voltage source such that a second current from the second voltage source flows between the third and fourth electrical connectors;
a first electrode electrically coupled to the first electrical connector;
a second electrode electrically coupled to the second electrical connector;
a third electrode electrically coupled to the third electrical connector; and
a fourth electrode electrically coupled to the fourth electrical connector, wherein the first and second electrodes are located between the third and fourth electrodes.

20. The implantable medical device of claim 19, wherein the first current is a stimulation current and the second current is a steering current that limits an outward reach of the stimulation current.

21. The implantable medical device of claim 20, wherein the stimulation current is a train of pulses and the steering current is a squarewave.

22. The implantable medical device of claim 20, wherein the steering current is present only when the stimulation current is present.

23. The implantable medical device of claim 20, wherein the first and second electrodes are present on a paddle, are rectangular, and have a first length and the third and fourth electrodes are present on the paddle, are rectangular, and have a second length that is more than twice the first length.

24. The implantable medical device of claim 20, further comprising:
a third voltage source not referenced to the first and second voltage sources;
a fifth and a sixth electrical connector referenced to the third voltage source such that a third current from the third voltage source flows between the fifth and sixth electrical connectors.

25. The implantable medical device of claim 24, wherein the lead further comprises:
a fifth electrode electrically coupled to the fifth electrical connector; and
a sixth electrode electrically coupled to the sixth electrical connector, the fifth and sixth electrodes being located between the first and second electrodes, the third current being a second steering current that increases an outward reach of the stimulation current.

26. The implantable medical device of claim 25, wherein the steering current and the second steering current have a frequency that is greater than a frequency of the stimulation current such that the steering current and the second steering current do not depolarize the tissue.

27. The implantable medical device of claim 20, wherein the steering current has a frequency that is greater than a frequency of the stimulation current such that the steering current does not depolarize the tissue.

28. The implantable medical device of claim 19, wherein the second current is a stimulation current and the first current is a steering current that increases an outward reach of the stimulation current.

29. The implantable medical device of claim 28, wherein the stimulation current is a train of pulses and the steering current is a squarewave.

30. The implantable medical device of claim 28, wherein the steering current is present only when the stimulation current is present.

31. The implantable medical device of claim 28, wherein the first and second electrodes are rectangular and have a first length and the third and fourth electrodes are rectangular and have a second length that is less than half of the first length.

32. The implantable medical device of claim 28, further comprising:
a third voltage source not referenced to the first and second voltage sources;
a fifth and a sixth electrical connector referenced to the third voltage source such that a third current from the third voltage source flows between the fifth and sixth electrical connectors.

33. The implantable medical device of claim 32, wherein the lead further comprises:
   a fifth electrode electrically coupled to the fifth electrical connector; and
   a sixth electrode electrically coupled to the sixth electrical connector, the first, second, third, and fourth electrodes being located between the fifth and sixth electrodes, the third current being a second steering current that limits an outward reach of the stimulation current.

34. The implantable medical device of claim 33, wherein the steering current and the second steering current have a frequency that is greater than a frequency of the stimulation current such that the steering current and the second steering current do not depolarize the tissue.

35. The implantable medical device of claim 28, wherein the steering current has a frequency that is greater than a frequency of the stimulation current such that the steering current does not depolarize the tissue.

36. The implantable medical device of claim 19, wherein the first, second, third, and fourth electrodes are concentric circles, with the third electrode having a smallest diameter and the fourth electrode having the largest diameter.

37. The implantable medical device of claim 19, wherein the first, second, third and fourth electrodes are ring electrodes along a body of the lead.

* * * * *